(12) United States Patent
Anderson et al.

(10) Patent No.: US 8,408,218 B2
(45) Date of Patent: Apr. 2, 2013

(54) APPLICATOR WITH EXTENDABLE IMPLEMENT

(75) Inventors: Dennis Jon Anderson, Randolph, NJ (US); Robert John Wilczynski, Perth Amboy, NJ (US); Michael Joseph Chervassi, Phillipsburg, NJ (US)

(73) Assignee: HCT Asia Ltd, Central (HK)

( * ) Notice: Subject to any disclaimer, the term of this patent is extended or adjusted under 35 U.S.C. 154(b) by 48 days.

(21) Appl. No.: 12/976,772

(22) Filed: Dec. 22, 2010

(65) Prior Publication Data

US 2011/0297173 A1 Dec. 8, 2011

Related U.S. Application Data

(60) Provisional application No. 61/351,409, filed on Jun. 4, 2010.

(51) Int. Cl.
  *A45D 40/26* (2006.01)
(52) U.S. Cl. ................. 132/218; 132/318; 132/320
(58) Field of Classification Search ............. 132/218, 132/318, 320; 401/127, 272, 274, 275, 279; 15/160
See application file for complete search history.

(56) References Cited

U.S. PATENT DOCUMENTS

| | | | |
|---|---|---|---|
| 4,165,755 A | 8/1979 | Cassai | |
| 4,428,388 A | 1/1984 | Cassai et al. | |
| 4,446,880 A | 5/1984 | Gueret et al. | |
| 4,545,393 A * | 10/1985 | Gueret et al. | 132/218 |
| 4,869,612 A | 9/1989 | Mooney et al. | |
| 5,137,038 A | 8/1992 | Kingsford | |
| 5,328,282 A | 7/1994 | Charrier et al. | |
| 6,145,514 A | 11/2000 | Clay | |
| 7,429,141 B2 | 9/2008 | Habatjou | |
| 8,141,561 B2 | 3/2012 | Thorpe et al. | |
| 2005/0249539 A1 | 11/2005 | Habatjou | |
| 2006/0162736 A1* | 7/2006 | Gray | 132/218 |
| 2009/0044357 A1 | 2/2009 | Chan et al. | |
| 2009/0071499 A1* | 3/2009 | Wyatt et al. | 132/218 |
| 2009/0097899 A1* | 4/2009 | Carroll | 401/109 |
| 2009/0194120 A1 | 8/2009 | Pires et al. | |
| 2009/0194127 A1 | 8/2009 | Pires et al. | |

FOREIGN PATENT DOCUMENTS

| | | |
|---|---|---|
| CN | 101884463 A | 11/2010 |
| DE | 10038850 A1 | 2/2002 |
| EP | 2084986 A2 | 8/2009 |
| EP | 2301379 A1 | 3/2011 |
| JP | 2007068945 A | 3/2007 |
| WO | WO9211785 A1 | 7/1992 |
| WO | WO2007117091 A1 | 10/2007 |
| WO | WO2010098997 A1 | 9/2010 |

OTHER PUBLICATIONS

The GB Search Report mailed Sep. 28, 2011 for GB patent application No. 1109399.4, 6 pages.
"Givenchy Demesure Audacious Lashes Mascara," May 17, 2011, retrieved from the internet at <<http://www.fashionizers.com/perfumes-makeup/givenchy-demesure-audacious-lashes-mascara/>>, 9 pages.
Non-Final Office Action for U.S. Appl. No. 12/399,591, mailed on May 10, 2011, James Thorpe, "Mascara Applicators," 9 pages.

* cited by examiner

*Primary Examiner* — Todd Manahan
*Assistant Examiner* — Brianne Kalach
(74) *Attorney, Agent, or Firm* — Lee & Hayes, PLLC

(57) ABSTRACT

An applicator system for applying a product to a surface includes an extendable implement comprising an applicator that is selectively extendable. By virtue of having an applicator that is selectively extendable, the extendable implement is capable of applying various products utilizing individual portions of the extendable implement to apply the product to hard-to-reach areas and to achieve multiple desired effects.

20 Claims, 8 Drawing Sheets

SECTION A-A

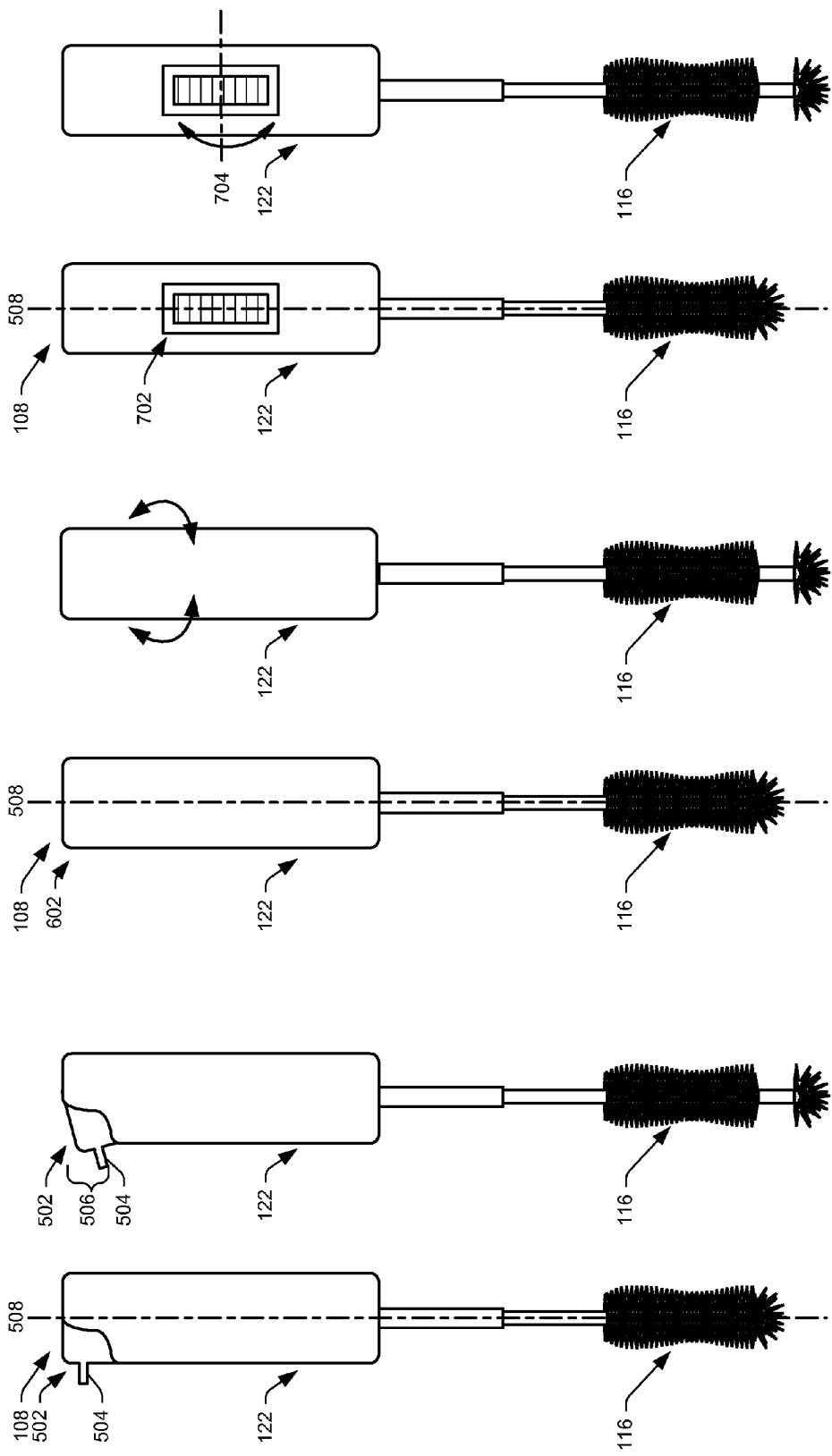

# APPLICATOR WITH EXTENDABLE IMPLEMENT

This application claims the benefit of U.S. Provisional Application No. 61/351,409, filed on Jun. 4, 2010, which is incorporated herein by reference in its entirety.

BACKGROUND

Devices exist for applying cosmetic or medicinal products to a body. Existing applicators are typically designed to apply mascara to eyelashes in one technique. For example, one applicator may have short, densely arrayed bristles and may be employed for applying mascara to eyelashes to achieve a desired effect (e.g., to volumize eyelashes). Another applicator may have longer, less densely arrayed bristles for applying mascara to eyelashes to achieve an alternative desired effect (e.g., to separate and define eyelashes). Still another applicator may be smaller so as to apply mascara to small areas (e.g., to corners of the eye).

However, existing applicators have limited functionality, and are not conducive to applying mascara to eyelashes using different techniques and/or to different regions of the eye. Accordingly, there remains a need in the art for improved applicator systems that allow application of mascara using different techniques and/or adjustments to achieve multiple desired effects.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 5A and FIG. 5B depict an illustrative side lever actuator in first and second positions.

FIG. 6A and FIG. 6B depict an illustrative rotating cap actuator in first and second positions.

FIG. 7A and FIG. 7B depict an illustrative dial actuator in first and second positions.

DETAILED DESCRIPTION

Overview

This application describes applicator systems and extendable implements comprising an applicator that is selectively extendable. By virtue of having an extendable implement, devices according to this disclosure are adaptable to apply various different cosmetic, medicinal, and/or personal care products to a body utilizing individual portions of the extendable implement to achieve multiple desired effects. For example, a user may apply mascara to a central region of the eyelashes while the applicator is in an un-extended position, or a user may apply mascara to a corner portion of the eyelashes while the applicator is in an extended position.

Generally, an applicator system according to this disclosure comprises a receptacle assembly and an extendable implement. The receptacle assembly includes a reservoir for containing a product to be dispensed and, in some implementations, may comprise a shell housing the reservoir. The extendable implement includes an applicator comprising a brush portion and a tip portion. The tip portion is extendably attached distal to the brush portion. Further, the tip portion may be stretchably extendable, slideably extendable, or extendable in some other manner. For example, the tip portion may be configured to stretchably extend at least about 8 millimeters (0.3 inches) linearly away from the brush portion. However, in other embodiments, the applicator may be extendible a greater or lesser distance (e.g., 4 millimeters to about 20 millimeters, or more). In addition to the applicator comprising an extendable tip portion, the extendable implement according to this disclosure generally comprises a cap with an actuator protectively disposed therein. A hollow stem houses a linkage, to which the actuator disposed in the cap is mechanically coupled, and the applicator is disposed on the stem opposite the cap.

In various embodiments, the extendable implements described herein may be actuated by any suitable actuation mechanism, such as, for example, an actuator disposed in a side portion of the cap or a top portion of the cap. Also, for example, the actuator may comprise a button, a lever, a dial, or a rotatable portion. Various embodiments of the applicator are also contemplated. For example, the applicator may comprise a brush, a sponge, and/or flocking. The extendable implement may be removably coupled to the receptacle assembly by a variety of attachment means, such as by snap fit, by screw threads, by a twist lock mechanism, by magnetic force, by interference fit, combinations of any of the foregoing, or the like.

Illustrative Applicator System with Adjustable Implement

Figure 1C:
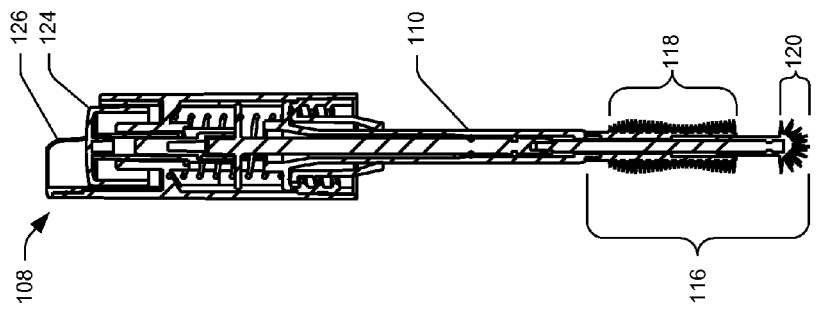
FIG. 1C depicts an illustrative extendable implement housed by the applicator system of FIG. 1A in an extended condition.
Figure 1B:
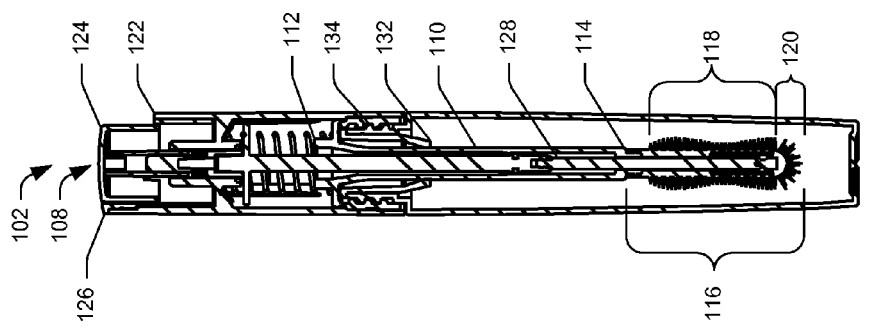
FIG. 1B depicts a cross-sectional view of the illustrative applicator system shown in FIG. 1A, taken along line A-A.
Figure 1A:
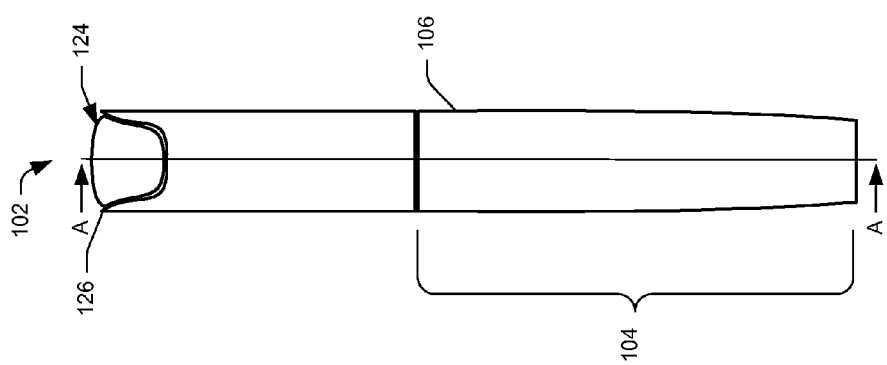
FIG. 1A depicts an illustrative applicator system for applying a product to a surface.

FIG. 1A depicts an illustrative applicator system 102, FIG. 1B depicts a respective cross sectional view A-A of the applicator system 102, and FIG. 1C depicts the extendable implement housed by the applicator system of FIG. 1A in the extended condition. The applicator system 102 includes a reservoir assembly 104 with a reservoir 106 for containing a cosmetic, medicinal, personal care, or other product. While in the illustrated embodiment, the receptacle assembly 104 is illustrated as comprising an opaque reservoir 106, in some implementations, the reservoir 106 may be made of clear plastic material, in which case, the contents of the reservoir may be visible. While FIG. 1A illustrates applicator systems 102 comprising reservoir 106, applicator system 102 may also comprise a shell (not shown) housing reservoir 106.

As illustrated, receptacle assembly 104 may comprise a substantially tube-shaped reservoir 106, which may be formed of plastic (e.g., polypropylene (PP), acrylonitrile butadiene styrene (ABS), Polyoxymethylene (POM)), glass, or any other suitable material, for containing a cosmetic, medicinal, personal care, or other product. Further, while receptacle assembly 104 is illustrated as a substantially tube-shaped assembly, a variety of receptacle shapes and types are contemplated. For example, the receptacle may be rectangular shaped, triangular shaped or any other suitable receptacle shape.

Additionally, section view A-A of the applicator system 102 is shown in FIG. 1B. FIG. 1B illustrates an extendable implement 108 of the applicator system 102. The extendable implement 108 comprises a hollow stem 110 having a top end 112 and a bottom end 114. The bottom end 114 of the stem 110 has an applicator 116 coupled thereto. In FIG. 1B applicator 116 comprises a brush 118 fixed to the bottom end 114 of hollow stem 110, and a tip 120 extendably attached distal to the brush 118. The applicator 116 may comprise a stretchably extendable tip, a slideably extendable tip, a telescopically extendable tip, or any other extendable tip. Further, while brush 118 is illustrated here as being generally a shaft-shaped unit of bristles for application of a product such as mascara, the extendable applicators according to this disclosure may also be used to apply other products, such as foundation, blush, or other cosmetic products and may take on other shapes, such as having a triangular cross section, a square cross section, a bulb shape, or the like. Likewise, while tip 120 is illustrated here as being a generally bulb-shaped unit of bristles for application of a product such as mascara, foundation, blush, or other cosmetic products, other shapes are also contemplated. For example, tip 120 may be mohawk-shaped, knife-shaped, mace-shaped or the like.

Extendable implement 108 is further shown to have a cap 122 securely disposed on the top end 112 of stem 110. The cap 122 has an actuator 124 that, in this example, comprises a top portion of cap 122 configured, as a push-button mechanism disposed on the top end of the cap 122 and at least partially surrounded by a ridge 126. However, alternative actuators are conceptualized. For example, actuator 124 may be a lever, a dial, a rotatable portion of cap, a squeezable portion of cap, or a switch mechanism. Further, while FIG. 1B illustrates a push-button mechanism that is partially surrounded by ridge 126, push-button mechanism may additionally or alternatively comprise a translucent over-molded cover and/or a light-emitting diode (LED), housed inside the push-button mechanism, that may light when the applicator is in the extended condition.

In the illustrated example, the actuator 124 is connected to a mechanical linkage 128 housed in the hollow stem 110. However, in other examples the actuator 124 may be connected to the applicator via a hydraulic mechanism, an electrical mechanism, a pneumatic mechanism, a magnetic mechanism, or the like. Referring to FIG. 1B, the linkage 128 is also mechanically connected to the applicator 116 disposed on the bottom end 114 of stem 110, thereby coupling both the actuator 124 and the applicator 116 such that the applicator 116 is selectively extendable to at least about 8 millimeters (0.3 inches) linearly to an extended position, as shown in FIG. 1C. In some embodiments, receptacle assembly 104 may include a wiper 132 which may be housed in a threaded collar 134 of reservoir 106. When included, the wiper 132 is configured to remove any excess product (e.g., mascara) from the applicator 116 when the adjustable implement 108 is removed to apply the product to a body (e.g., eyelashes). For each embodiment, the applicator is described in the context of an applicator for applying a mascara product to eyelashes. However, it should be understood that applicators as described herein may be used and adapted to apply other products and may be used to apply product to other portions of the body.

The applicator system 102 provides for the application of mascara to eyelashes at least utilizing two individual portions of the extendable implement (i.e., the brush 118 and the tip 120). This linear extension enables a user to apply mascara with a single applicator system 102 rather than multiple different applicators. Specifically, the applicator system 102 enables the user to apply mascara with a single applicator, such as the extending applicator 116 rather than using two distinctly shaped applicators to apply the mascara to different areas of a body (e.g., using the brush to apply product to a central region of an eyelash and using the tip to apply product to corners of an eyelash).

In one specific embodiment, with the extendable implement 108 configured to selectively extend the applicator 116 about 8 millimeters (0.3 inches) to a linearly extended position, the user may first apply the mascara to the eyelashes using the brush 118 and the tip 120 as a unitary applicator while the applicator 116 is not extended (shown in FIG. 1B). The user can then selectively extend the applicator 116 to the linearly extended position (shown in FIG. 1C) and apply the product to corners of the eyelashes, or other hard to reach areas using only the tip 120 of the applicator 116. In the embodiment shown in FIGS. 1B and 1C, extension of the tip 102 results in a gap between the tip and the brush that is substantially void of bristles. However, in other embodiments, bristles may be provided in the gap between the brush and the tip.

Figure 2:
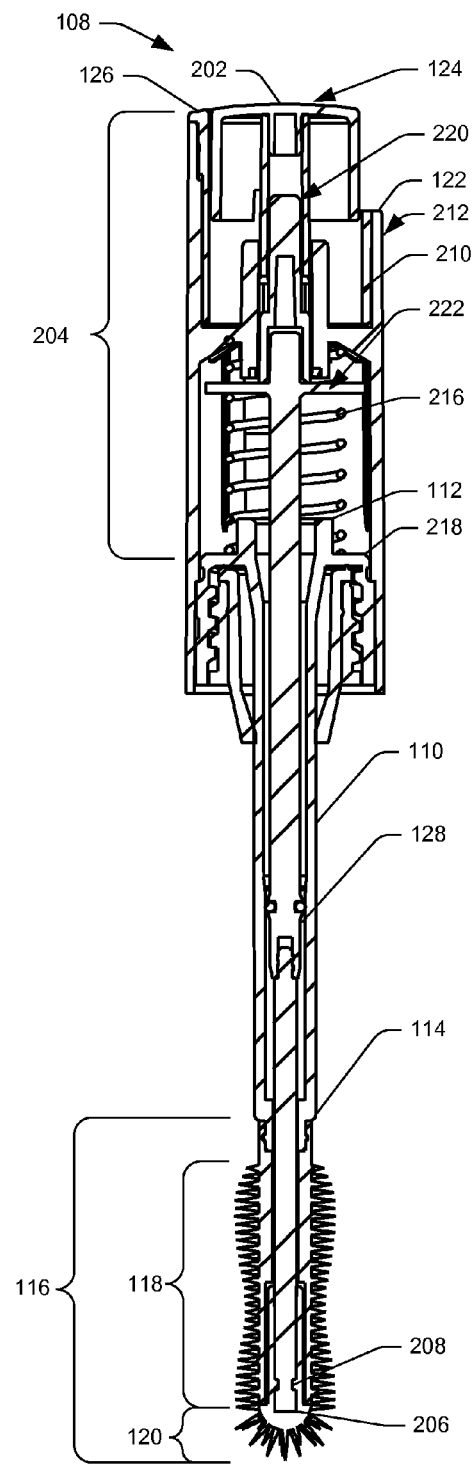
FIG. 2 is an enlarged cross-sectional view showing additional details of the illustrative extendable implement of FIG. 1C.

FIG. 2 is an enlarged section view of the extendable implement 108 shown in FIG. 1B. The extendable implement 108 shown in FIG. 2 presents some of the same components shown in both FIG. 1B and FIG. 1C in greater detail. For instance, the adjustable implement shown in FIG. 2 illustrates hollow stem 110, top end 112, bottom end 114, applicator 116, cap 122, linkage 128 and actuator 124. FIG. 2 further shows additional details of the mechanical interconnection of a push-button 202 to a click-pen mechanism 204 housed by the cap 122. FIG. 2 also illustrates in more detail the mechanical interconnection of the linkage 128 coupled to tip 120 of applicator 116 via an applicator insert 206. While applicator insert 206 is shown here in FIG. 2 to have a slot 208 that is configured to receive and securely hold illustrative tip 120 (e.g., bulb-shaped unit with bristles), additional alternative fastening mechanisms or techniques are contemplated. For example, applicator insert 206 may be configured to receive and securely hold a tip 120 by way of adhesive, fasteners, threads, or the like. Further, applicator insert 206 and tip 120 may be configured to be over-molded as a single unit. Here, tip 120 is shown as a bulb-shaped unit of bristles, however tip 120 could be mohawk-shaped, knife-shaped, mace-shaped or any other suitable applicator shape. Also shown in FIG. 2 is a ring 210 securely fixed to a top end 212 of cap 122. Ring 210 comprises the ridge 126 that protectively surrounds push-button 202 and is configured to prevent the push-button 202 from inadvertently being actuated (e.g., while in a purse of a user). Ring 210 may be securely fixed to top end 212 of cap 122 via press fit, snap fit, adhesive, fasteners threads or any other suitable fastening means.

FIG. 2 illustrates click-pen mechanism 204 mechanically interconnecting push-button 202 and linkage 128. Generally, click-pen mechanism 204 comprises a spring 216, an inner cap 218, and a twist/elevator assembly 220 that when assembled into the cap 122 provides a push click and a push un-click functionality. As illustrated in FIG. 2, push-button 202 is disposed on twist/elevator assembly 220, and twist/elevator assembly 220 is configured to be disposed on a top 222 of linkage 128. Hence, when the push-button 202 is pushed, push-button 202 linearly displaces twist/elevator assembly 220 and linkage 128, and compresses spring 216. The displaced push-button 202 then clicks the tip 120 into the extended position. Likewise, when the push-button 202 is again displaced, push-button 202 compress spring 216 to un-click tip 120, which allows spring 216 to linearly displace linkage 128 back into un-extended position.

Additionally, while FIG. 2 shows extendable implement 108 with a push-button actuator 202, other actuators are contemplated that may be used in the arrangement of components shown in FIG. 2 to displace the linkage 128 and linearly extend applicator 116. For example, extendable implement 108 may comprise a lever actuator disposed on a side portion of cap 122 that moves linkage 128 and applicator 116, or extendable implement 108 may comprise a dial disposed on a side portion of cap 122 that moves linkage 128 and applicator 116, or extendable implement 108 may comprise a rotatable portion of cap 122 that moves linkage 128 and applicator 116. Further, it is contemplated that these actuators may comprise an indicator, which, when the implement is extended, indicates to the user that the applicator is either in the un-extended condition or extended condition. For example, the indicator may be a red sheath arranged along an inside portion of the ring 210 and disposed proximate to the ridge 126. In this embodiment, the indicator (i.e., a red sheath) may be configured to be visible when the actuator is displaced, thereby exposing the indicator.

In the embodiment of FIG. 2, extendable implement 108 comprises a push-button actuator 202 mechanically interconnected with click-pen mechanism 204. While FIG. 2 shows push-button actuator 202 mechanically interconnected with click-pen mechanism 204 housed in cap 122, other types of mechanical interconnections are contemplated. For example, push-button actuator 202 may be mechanically interconnected with linkage 128 via a pressurized rubber bulb that when squeezed by push-button actuator 202 displaces linkage 128, or any other displacing device. Further, while FIG. 2 shows extendable implement 108 comprising a push-button actuator 202 mechanically interconnected with click-pen mechanism 204 housed in cap 122, extendable implement 108 may further comprise a locking mechanism to prevent the actuator 124 from inadvertently extending tip 120 from the un-extended position. Similarly, extendable implement 108 may also or alternatively further comprise a trip mechanism to cause the actuator 124 to retract the tip 120 from the extended position when the extendable implement 108 is placed in the reservoir 106 in an extended condition.

As illustrated, extendable implement 108 may comprise a tubular cap 122, hollow stem 110, tubular linkage 128, and an applicator insert 206 that may be formed of plastic (e.g., polypropylene (PP), acrylonitrile butadiene styrene (ABS), Polyoxymethylene (POM)), metal, or any other suitable material. Likewise, bulb-shaped tip 120 may be formed of rubber, low density polyethylene (LDPE), thermoplastic elastomers (TPE), silicone, plastic (e.g. polypropylene (PP)), fabric mesh, or any other suitable material. Furthermore, bulb-shaped tip 120 may be formed integrally with bristles as an injection molded unit, as a series of installed bristles (e.g., like a toothbrush), as a series of tied bristles (e.g., like a pipe cleaner), or other configuration. Furthermore, it is contemplated that shaft-shaped brush 118 may be formed of rubber, low density polyethylene (LDPE), thermoplastic elastomers (TPE), silicone, plastic (e.g. polypropylene (PP)), fabric mesh, or any other suitable material. Similarly, it is also contemplated that shaft-shaped brush may be formed integrally with bristles as an injection molded unit, as a series of installed bristles (e.g., like a toothbrush), as a series of tied bristles (e.g., like a pipe cleaner), or other configuration. Further, bulb-shaped tip 120 may be over-molded to shaft-shaped brush 118 as a single unit. Alternatively, rather than over-molding a tip 120 to a brush 118, both the tip 120 and the brush 118 comprising bristles, instead, another body comprising bristles may be over-molded to an over-molded brush and tip unit without bristles. Further, tip 120 may not be over-molded to the brush 118, and instead, as discussed above, the tip 120 may be over-molded to the applicator insert 206. Here, again, another body comprising bristles may be over-molded to the tip 120 and the brush 118 that are without bristles.

Figure 3A:
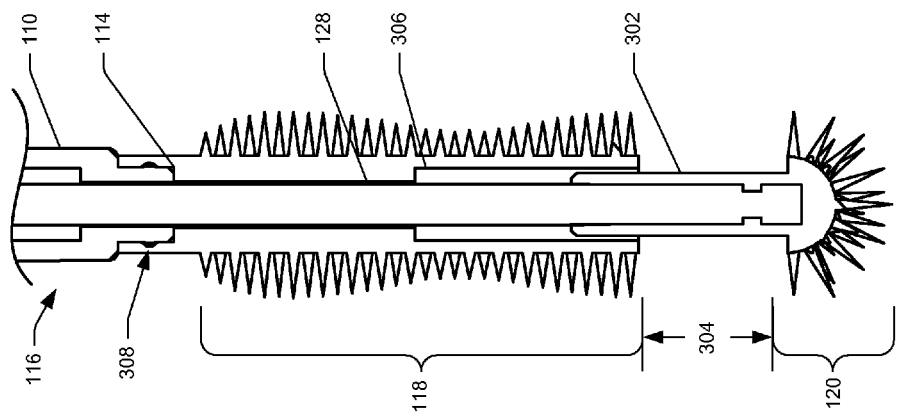
FIG. 3A and FIG. 3B depict illustrative detail section views of a slideable applicator of the extendable implement of FIG. 1B in non-extended (3A) and extended (3B) positions.
Figure 3B:
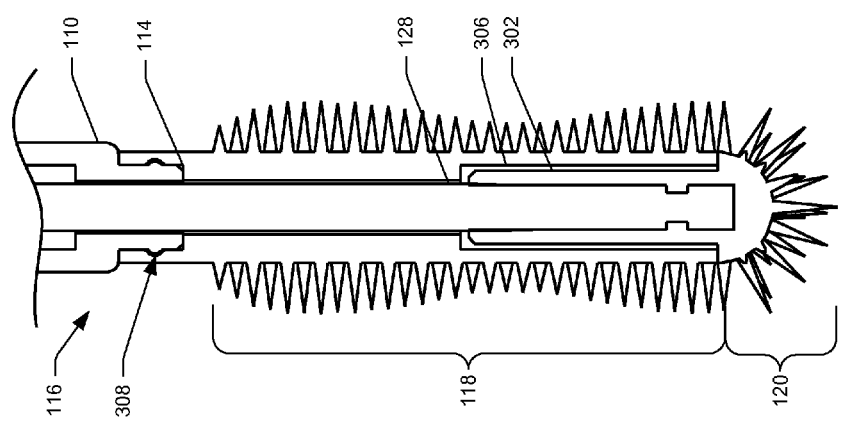

FIG. 3A and FIG. 3B illustrate detail section views of a slideable applicator 116 of the extendable implement 108 in non-extended (3A) and extended (3B) positions. In this example, a slideable shaft 302 of tip 120 facilitates the extending of the tip 120 a distance 304 linearly from the brush 118 when actuator 124 is actuated. While the slideable shaft 302 is depicted generally as a tubular rod substantially fixed to tip 120, in other embodiments, the slideable shaft 302 may be configured in any other suitable shape, size and configuration. For example, and as discussed above, tip 120 may be mohawk-shaped, knife-shaped, mace-shaped or any other suitable applicator shape. For example, slideable shaft 302 may be knife-shaped or rectangular bar shaped, or any other suitable shape to provide for linkage 128 to displace slideable shaft 302 from the un-extended position to the extended position and vice versa. Likewise, brush 118 is illustrated as comprising a cavity 306 having a shape complimentary to that of the slideable shaft 302 for receiving and guiding slideable shaft 302 from the un-extended position to the extended position and vice versa. Further, it follows that, cavity 306 may also be knife-shaped or rectangular bar shaped, or any other suitable shape to provide for linkage 128 to displace slideable shaft 302 from the un-extended position to the extended position and vice versa.

In one embodiment, as shown in FIG. 3A and FIG. 3B, brush 118 is illustrated to be fixed to the bottom end 114 of stem 110 by a snap fit 308. However, it is also contemplated that brush 118 may be fixed to the bottom end 114 of stem 110 by press fit, adhesive, fasteners, threads, over-molding, or any other suitable fastening means.

Figure 4A:
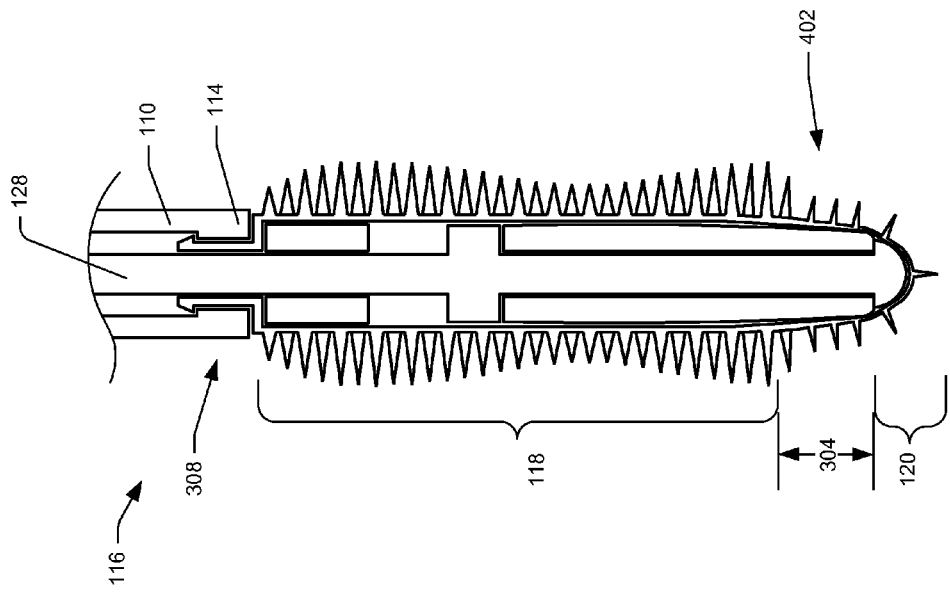
FIG. 4A and FIG. 4B depict illustrative detail section views of a stretchable applicator of the extendable implement of FIG. 1B in non-extended (4A) and extended (4B) positions.
Figure 4B:
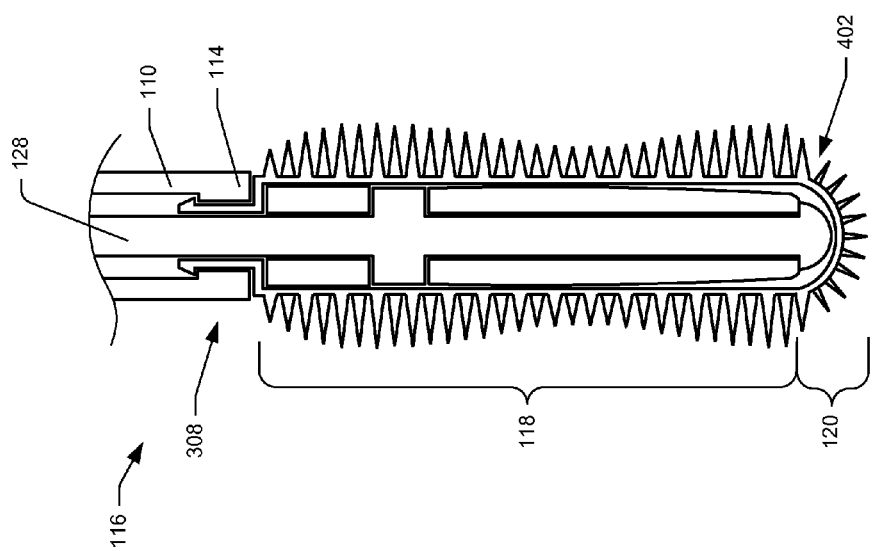

FIG. 4A and FIG. 4B illustrate detail section views of a stretchable applicator 116 of the extendable implement 108 in non-extended (4A) and extended (4B) positions. In this example, a stretchable portion 402 disposed between the tip 120 and the brush 118 facilitates the extending of the tip 120 a distance 304 linearly from the brush 118 when actuator 124 is actuated. While the stretchable portion 402 is shown in this embodiment as an area disposed between the tip 120 and the brush 118, in other embodiments, stretchable portion 402 may include one or more extra folds of material sandwiched between the tip 120 and the brush 118. Moreover, while the stretchable portion 402 is shown in this figure as having one or more bristles located thereon, in other embodiments, the stretchable portion may be free of bristles.

FIGS. 5A and 5B, FIGS. 6A and 6B, and FIGS. 7A and 7B depict three illustrative extendable implements that may be used with receptacle assembly 104 of FIG. 1, each having different actuators 124. FIGS. 5A and 5B illustrate an extendable implement with a lever actuator 502. FIGS. 6A and 6B illustrate an extendable implement with a rotatable actuator 602. FIGS. 7A and 7B illustrate an extendable implement with a dial actuator 702.

FIG. 5A and FIG. 5B illustrate side lever actuator 502 having a lever 504 that protrudes slightly from a surface of the cap 122. FIG. 5A illustrates side lever actuator 502 before a user displaces the side lever actuator 502. Lever 504 is configured to be displaced a distance 506 towards the applicator 116. Additionally, FIG. 5A further illustrates the applicator 116 in the un-extended position, before lever 504 is displaced the distance 506 axially relative to longitudinal axis 508 of extendable implement 108. Upon being displaced the distance 506, lever 504 is illustrated in FIG. 5B as being temporarily displaced toward applicator 116. Likewise, FIG. 5B further illustrates the applicator 116 in the extended position as a result of the lever 504 being displaced axially relative to the longitudinal axis 508 of the extendable implement 108. While FIGS. 5A and 5B illustrate a lever 504 other mechanical means are contemplated. For example a raised bump, a detent, or any other means to enable a user to selectively displace the side lever actuator 502 axially relative to longitudinal axis 508 of the extendable implement 108. A locking mechanism (not shown) may be produced by pushing the lever 504 in a transverse direction into a receptacle or groove (also not shown) in the cap 122. Further, as discussed above, a ridge (not shown) may also be disposed on the cap 122 and arranged around the lever actuator 502 to protect the lever actuator and keep it from being inadvertently actuated.

FIGS. 6A and 6B illustrate a rotating actuator 602. Here, the rotating actuator 602 is configured to be rotatable about longitudinal axis 508 of the extendable applicator 108. FIG. 6B illustrates rotating actuator 602 being displaced rotationally about longitudinal axis 508 in both a clockwise direction, and a counter-clockwise direction. FIG. 6A further illustrates applicator 116 in un-extended position, before rotating actuator 602 is displaced rotationally about longitudinal axis 508. Upon being displaced rotationally, applicator 116 extends to the extended position shown in FIG. 6B. While FIGS. 6A and 6B illustrate the entire cap 122 rotating about longitudinal axis 508, in other embodiments, a portion of the cap 122 (e.g., a middle portion of the cap or a top portion of the cap) may rotate about longitudinal axis 508.

FIGS. 7A and 7B illustrate a dial actuator 702. Here, the dial actuator 702 comprises a rotatable dial exposed on a side of the cap 122. The dial actuator 702 is configured to be rotatable about an axis 704 transverse to longitudinal axis 508 of the extendable applicator. FIG. 7A illustrates applicator 116 in un-extended position, before dial actuator 702 is displaced rotationally about axis 704. Upon being displaced in either the clockwise direction or the counter-clockwise direction, applicator 116 extends to the extended position shown in FIG. 7B.

While FIGS. 5A and 5B, FIGS. 6A and 6B, and FIGS. 7A and 7B, depict three illustrative extendable implements, each having different actuators 124, other types of actuators are also possible.

Illustrative Applicators

Figure 8:
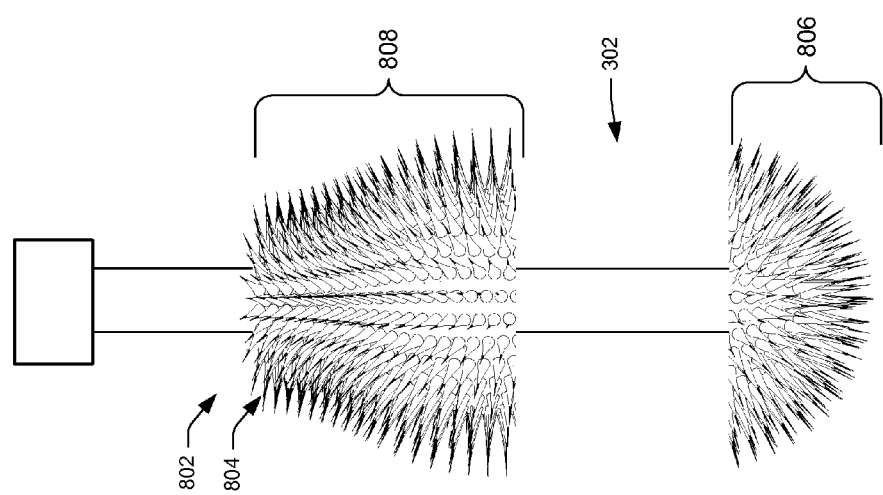
FIG. 8 depicts an illustrative extendable applicator that is a mace-shaped applicator with bristles.

FIG. 8, FIG. 9, FIG. 10A, FIG. 10B, and FIG. 10C depict five illustrative types of applicators 116, each extendably coupled to an extendable implement 108 and illustrated in an extended position. While, FIG. 8, FIG. 9, FIG. 10A, FIG. 10B, and FIG. 10C illustrate the five types of applicators 116 as being slideably extendable (i.e., comprising a slideable shaft 302), the five applicators illustrated in FIG. 8, FIG. 9, FIG. 10A, FIG. 10B, and FIG. 10C may alternatively be configured to be stretchably extendable (i.e., comprising a stretch able portion 402). The applicator 116 shown in FIG. 8 is a mace-shaped applicator 802 with bristles 804. The bristles 804 may comprise multiple columns, each column having a different bristle length. The different columns of bristle lengths may be staggered to increase the density of the bristles. Additionally, mace-shaped applicator 802 may comprise a dome-shaped tip 806 extendably attached distal to a cylindrical-shaped brush 808. Further, mace-shaped applicator 802 may be used by a user while the mace-shaped applicator 802 is in un-extended position or in extended position. The un-extended position of the mace-shaped applicator 802 may support eyelash volume, while the extended position of the mace-shaped applicator 802, having the dome-shaped tip 806 extend out and away from the cylindrical-shaped brush 808, may support eyelash separation and definition and/or may be used to reach corners or other hard to reach locations.

Figure 9:
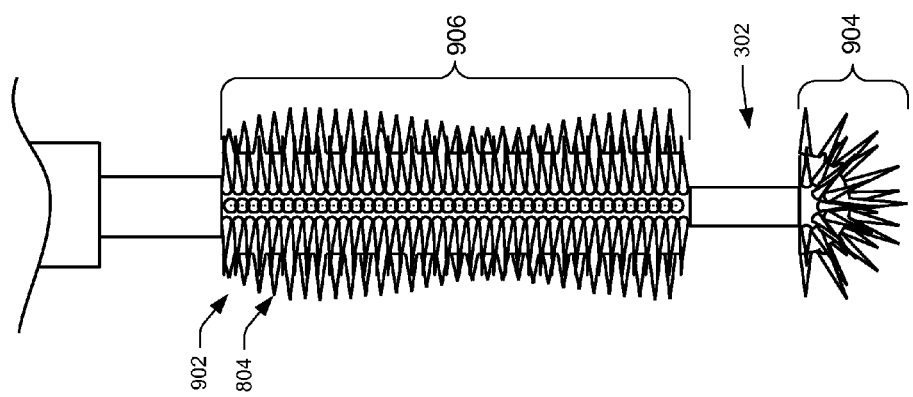
FIG. 9 depicts an illustrative extendable applicator that is a rod-shaped applicator with bristles.

With respect to FIG. 9, the applicator 116 is a rod-shaped applicator 902, again with bristles 804. Similarly, here the bristles 804 may comprise multiple columns, each column having a different bristle length. Again, the different columns of bristle lengths maybe staggered to increase the density of the bristles. The rod-shaped applicator 902 may comprise a bulb-shaped tip 904 extendably attached distal to a shaft-shaped brush 906. Further, rod-shaped applicator 902 may be used by a user while the rod-shaped applicator 902 is in an un-extended position or in an extended position. The un-extended position of the rod-shaped applicator 902 may also support eyelash volume, while the extended position of the rod-shaped applicator 902, having the bulb-shaped tip 904 extend out and away from the shaft-shaped brush 906, may support eyelash separation and definition and/or may be used to reach corners or other hard to reach locations.

Figure 10A:
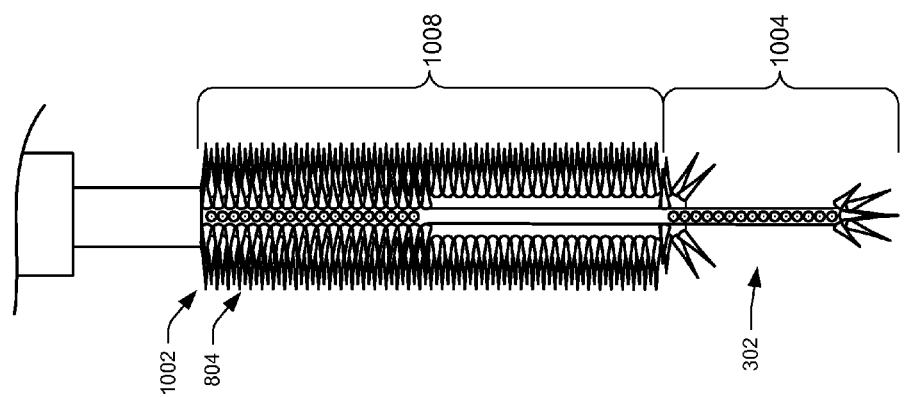
FIG. 10A, FIG. 10B, and FIG. 10C depict an illustrative extendable applicator that is also a rod-shaped applicator with bristles and a mohawk-shaped tip (FIG. 10B) or a knife-shaped tip (FIG. 10C).
Figure 10B:
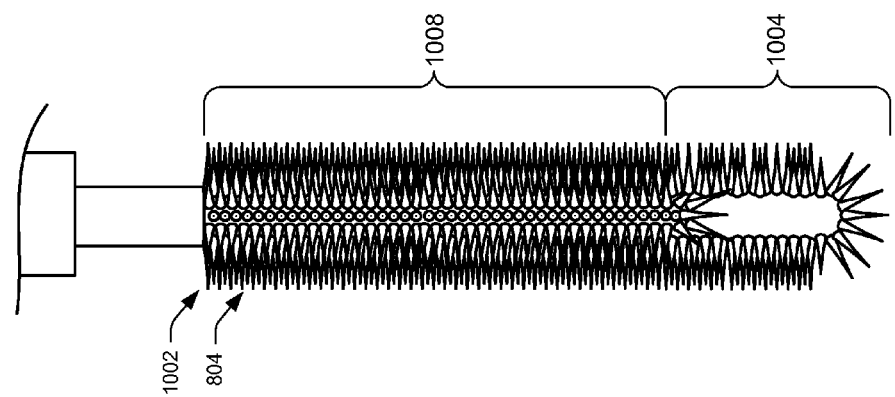
Figure 10C:
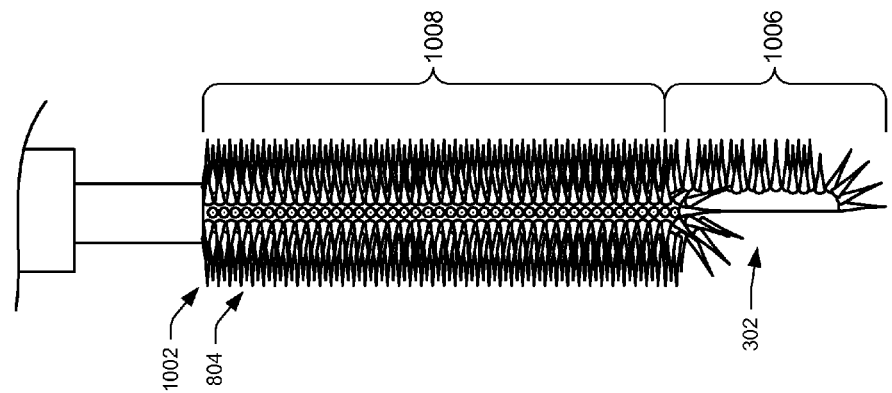

FIG. 10A, FIG. 10B, and FIG. 10C illustrate the applicator 116 as a rod-shaped applicator 1002 and bristles 804. FIG. 10B and FIG. 10C illustrate the applicator rod-shaped applicator 1002 in a side view position. Similarly, here the bristles 804 may comprise multiple columns, each column having a different bristle length and wherein the different columns of bristle lengths are staggered to increase the density of the bristles. Here, in this configuration, the rod-shaped applicator 1002 may comprise either a mohawk-shaped tip 1004, as illustrated in FIG. 10A and FIG. 10B, or a knife-shaped tip 1006, as illustrated in FIG. 10C, each extendably housed by a shaft-shaped brush 1008. Similarly, as discussed above, rod-shaped applicator 1002 may be used by a user while the rod-shaped applicator 1002 is in un-extended position or in extended position. The un-extended position of the rod-shaped applicator 1002 may support eyelash volume, while the extended position of the rod-shaped applicator 1002, having the knife-shaped tip 1004, or the knife-shaped tip 1004 extend out and beyond the shaft-shaped brush 1008, may support eyelash separation and definition and/or may be used to reach corners or other hard to reach locations.

While multiple embodiments of applicators 116 have been described above, it should be appreciated that the tips 120 and brushes 118 comprising the multiple embodiments of applicators 116 may be formed of rubber, low density polyethylene (LDPE), thermoplastic elastomers (TPE), silicone, plastic (e.g. polypropylene (PP)), fabric mesh, or any other suitable material.

Exemplary Method of Using Adjustable Implement

Figure 11:
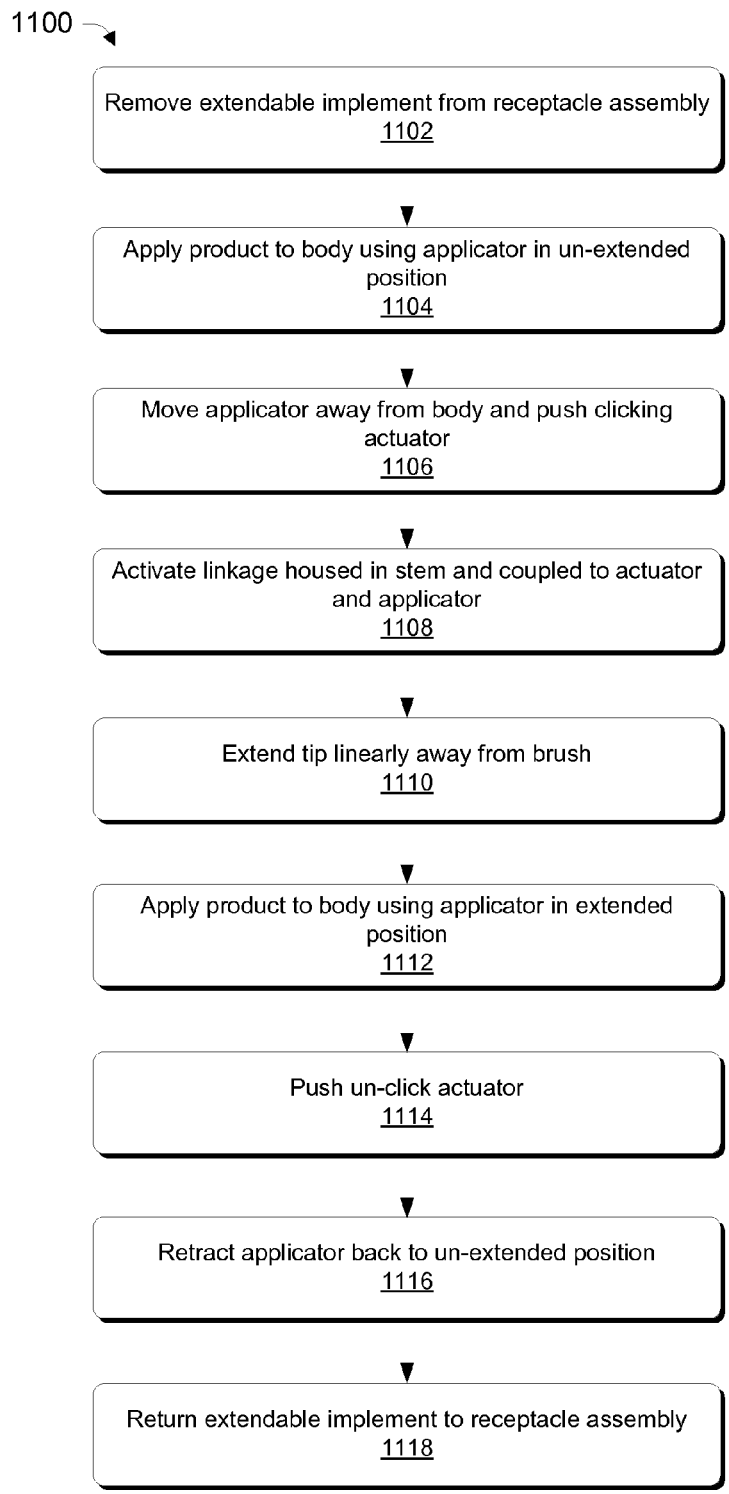
FIG. 11 is a flow diagram of an illustrative process for using the extendable implement.

FIG. 11 is a flow diagram of an example process 1100 which may, but need not necessarily be performed using the extendable implement 108 of FIG. 1. For convenience, the process 1100 will be described with reference to the extendable implement 108, but the process 1100 is not limited to use with this implement. For instance, a user may perform this process 1100 to apply mascara to eyelashes, or a user may perform this process to remove a substance from a body. In some instances, the user may perform this process in a manufacturing environment, in a commercial environment (e.g., beauty salon), or in a place of residence. While FIG. 11 illustrates a process 1100 for applying product to eyelashes, it is to be appreciated that this process may apply to applying any type substances to any type of body (e.g., applying touch-up paint to a vehicle).

Process 1100 includes an operation 1102, which represents removing an extendable implement (108) from a receptacle assembly (104). Next, operation 1104 represents applying mascara to eyelashes using an applicator (116) in an un-extended position (e.g., as shown in FIG. 1B) to achieve a desired effect (i.e., eyelash volume). Operation 1104 is followed by operation 1106, which represents moving the extendable implement away from the eyelashes and displacing an actuator (124) (e.g., by clicking a push button). Here, as discussed above with respect to FIGS. 5A and 5B, FIGS. 6A and 6B, and FIGS. 7A and 7B, the actuator could be displaced laterally, axially, rotatably, or in any other direction. As discussed above, the actuator may in some embodiments comprise a push-button (202). Next, process 1100 proceeds to operation 1108, which represents the displaced actuator activating a linkage (128) housed in a hollow stem (110), coupled to the actuator and applicator, wherein the applicator comprises a brush (118) and a tip (120) extendably attached distal to the brush. Operation 1108 is followed by operation 1110, which represents extending the tip to an extended position. Following the extending of the tip, the tip may be locked in the extended position (e.g., as shown in FIG. 1C. Process 1100 continues with operation 1112, which represents applying mascara to the eyelashes using the applicator in the extended position to achieve a desired effect (i.e., separation and definition). At operation 1114, a user deactivates the actuator (e.g., by unclicking), after which, at operation 1116, the tip retracts back to its un-extended position. Finally, process 1100 is complete when, at operation 1118, a user may return the extendable implement to receptacle assembly 104. Alternatively, in some embodiments, if the user returns the extendable implement to the receptacle without first retracting the applicator, a trip mechanism of the implement may automatically retract the applicator when the implement is inserted in the receptacle.

CONCLUSION

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. For example, in various embodiments, any of the structural features and/or methodological acts described herein may be rearranged, modified, or omitted entirely. For example, the shape, size, and configuration of the reservoir, cap, and extendable implement may be varied.

What is claimed is:

1. An extendable applicator system for applying a product to a surface, the extendable applicator system comprising:
an extendable implement comprising:
a stem having a top end and a bottom end, a first axis extending from the top end to the bottom end;
an applicator comprising a brush and a tip attached to the brush, the brush extending between a proximal and distal end, the proximal end attached to the bottom end of the stem, and the tip is extendably attached at the distal end of the brush, the tip comprising a plurality of bristles and at least some of the plurality of bristles of the tip extending in a direction parallel to the first axis;
a cap having a top end and a bottom end, the bottom end of the cap being securely disposed on the top end of the stem;
a push-button disposed on the top end of the cap and coupled to a linkage that extends through the entire applicator between a first end and a second end, the second end remote from the stem;
a tip insert attached to the second end of the linkage, the tip insert carrying the tip; the tip comprising a proximal end and a distal end, where the proximal end of the tip abuts the distal end of the brush in an un-extended position;
the push-button for selectively extending the tip into an extended position relative to the brush, creating a gap between the distal end of the brush and the proximal end of the tip, the gap being free of any bristles in order to facilitate application of the product to portions of the surface; and
a receptacle assembly for receiving the extendable implement.

2. The applicator system according to claim 1, wherein the push-button is configured to push the tip into the extended position in response to a first actuation of the push-button and to retract the tip into the un-extended position in response to a second actuation of the push-button.

3. The applicator system according to claim 2, further comprising a locking mechanism to prevent the push-button from inadvertently extending the tip from the un-extended position.

4. The applicator system according to claim 1, wherein the brush comprises a bulb-shaped unit of bristles over-molded to a shaft-shaped unit of bristles, and wherein the bulb-shaped unit of bristles is stretchably extendable from the shaft-shaped unit of bristles.

5. The applicator system according to claim 1, wherein the extended position of the tip is at least about 8 millimeters (0.3 inches) linearly from the brush.

6. The applicator system according to claim 1, wherein the tip is stretchably extendable from the brush, wherein the brush is over-molded to the stem.

7. The applicator system according to claim 6, wherein the tip is over-molded to the brush.

8. The applicator system according to claim 7, wherein the tip is a bulb-shaped unit of bristles and wherein the brush is a shaft-shaped unit of bristles, and wherein a diameter of the tip is smaller than a diameter of the brush to facilitate access to smaller areas of the body.

9. The applicator system according to claim 1, wherein the product comprises mascara.

10. An extendable implement for applying a product to a surface, the extendable implement comprising:
a stem having a top end and a bottom end;
an applicator fixed to the bottom end of the stem, the applicator comprising:
a first portion of bristles, the first portion of bristles extending between a proximal and distal end, the proximal end attached to the bottom end of the stem;
a cap securely disposed on the top end of the stem;
an actuator coupled to the cap, the actuator comprising a linkage that extends through the entire applicator between a first end and a second end, the second end remote from the stem;
a tip attached to the second end of the linkage, the tip carrying a second portion of bristles; the second portion of bristles comprising a proximal end and a distal end, where the proximal end of the second portion of bristles abuts the distal end of the first portion of bristles in an un-extended position;

the actuator configured for selectively extending the second portion of bristles into an extended position relative to the first portion of bristles, creating a gap between the proximal end of the second portion of bristles and the distal end of the first portion of bristles, the gap being free of any bristles in order to facilitate application of the product to portions of the surface, the actuator further comprising:

a mechanism that, in response to a first actuation of the actuator, extends the second portion of bristles into the extended position, and in response to a second actuation of the actuator, retracts the second portion of bristles into the un-extended position.

11. The extendable implement according to claim 10, wherein the applicator comprises a brush, a sponge, or flocking.

12. The extendable implement according to claim 11, wherein the second portion of bristles is stretchably extendable from the first portion of bristles, and wherein the second portion of bristles is over-molded to the first portion of bristles.

13. The extendable implement according to claim 10, wherein the actuator comprises a button, a lever, a dial, or a rotatable portion of the cap.

14. The extendable implement according to claim 13, wherein the actuator is at least partially surrounded by a portion of the cap.

15. The extendable implement according to claim 10, wherein the extended position of the second portion of bristles is at least about 8 millimeters (0.3 inches) linearly from the first portion of bristles.

16. An extendable applicator comprising:
a stem having a top end and a bottom end;
a brush extending between a proximal and distal end, the proximal end fixed to the bottom end of the stem, the brush having a tip attached at the distal end of the brush;
a cap disposed on the top end of the stem;
an actuator coupled to the cap, the actuator comprising a linkage that extends through the entire brush between a first end and a second end, the second end remote from the stem;
a tip insert attached to the second end of the linkage, the tip insert carrying the tip; the tip comprising a proximal end and a distal end, where the proximal end of the tip abuts the distal end of the brush in an un-extended position;
the actuator for selectively extend the tip into an extended position relative to the brush, creating a gap between the distal end of the brush and the proximal end of the tip, the gap being free of any bristles.

17. The extendable applicator according to claim 16, wherein the extended position of the tip is at least about 8 millimeters (0.3 inches) linearly from the brush.

18. The extendable applicator according to claim 16, wherein the actuator comprises a button, a lever, a dial, or a rotatable portion of the cap.

19. The extendable applicator according to claim 16, wherein the brush comprises a bulb-shaped unit of bristles over-molded to a shaft-shaped unit of bristles, and wherein the bulb-shaped unit of bristles is stretchably extendable from the shaft-shaped unit of bristles.

20. The extendable applicator according to claim 16, wherein the actuator comprises a button disposed in the cap and at least partially protectively surrounded by a ridge of the cap, the ridge arranged around at least a portion of the cap and configured to prevent the button from inadvertently being actuated.

* * * * *